(12) United States Patent
Davis et al.

(10) Patent No.: US 6,757,060 B2
(45) Date of Patent: Jun. 29, 2004

(54) OPTICAL PROBE FOCUSING APPARATUS AND METHOD

(75) Inventors: Kevin Davis, Ann Arbor, MI (US); Joseph B. Slater, Dexter, MI (US)

(73) Assignee: Kaiser Optical Systems, Ann Arbor, MI (US)

( * ) Notice: Subject to any disclaimer, the term of this patent is extended or adjusted under 35 U.S.C. 154(b) by 0 days.

(21) Appl. No.: 10/350,499

(22) Filed: Jan. 24, 2003

(65) Prior Publication Data

US 2003/0142303 A1 Jul. 31, 2003

Related U.S. Application Data

(60) Provisional application No. 60/351,731, filed on Jan. 25, 2002.

(51) Int. Cl.[7] .................................................. G01J 3/44
(52) U.S. Cl. ....................................... 356/301; 356/624
(58) Field of Search ................................. 356/301–303, 356/306, 614, 624; 250/459.1; 381/116

(56) References Cited

U.S. PATENT DOCUMENTS 5,920,385 A * 7/1999 Rossiter ........................ 356/73
6,067,156 A * 5/2000 Slater et al. ................. 356/301
6,603,545 B2 * 8/2003 Slater ........................... 356/301

* cited by examiner

*Primary Examiner*—Frank G. Font
*Assistant Examiner*—Layla Lauchman
(74) *Attorney, Agent, or Firm*—Gifford, Krass, Groh, Sprinkle, Anderson & Citkowski, PC

(57) ABSTRACT

Disclosed is a method of positioning a focused image within a sampled medium in an optical measurement probe of the type wherein a focused sampling image is transmitted through a window having a surface facing a sampled medium. A test medium is measured, preferably through the window, and the magnitude of an optical signal associated with the test medium is then compared to the magnitude of an optical signal associated with the window, and the result of the comparison is used to position the focused image. Typically, the magnitudes of optical signals are representative or Raman scattering or another wavelength-selective radiative sampling process such as fluorescence detection. The method is not limited in terms of window composition, and is compatible with sapphire windows commonly used in industry. Nor is the invention limited in terms of test medium though, in the preferred embodiment a fluid hydrocarbon such as isopropyl alcohol is used.

21 Claims, 1 Drawing Sheet

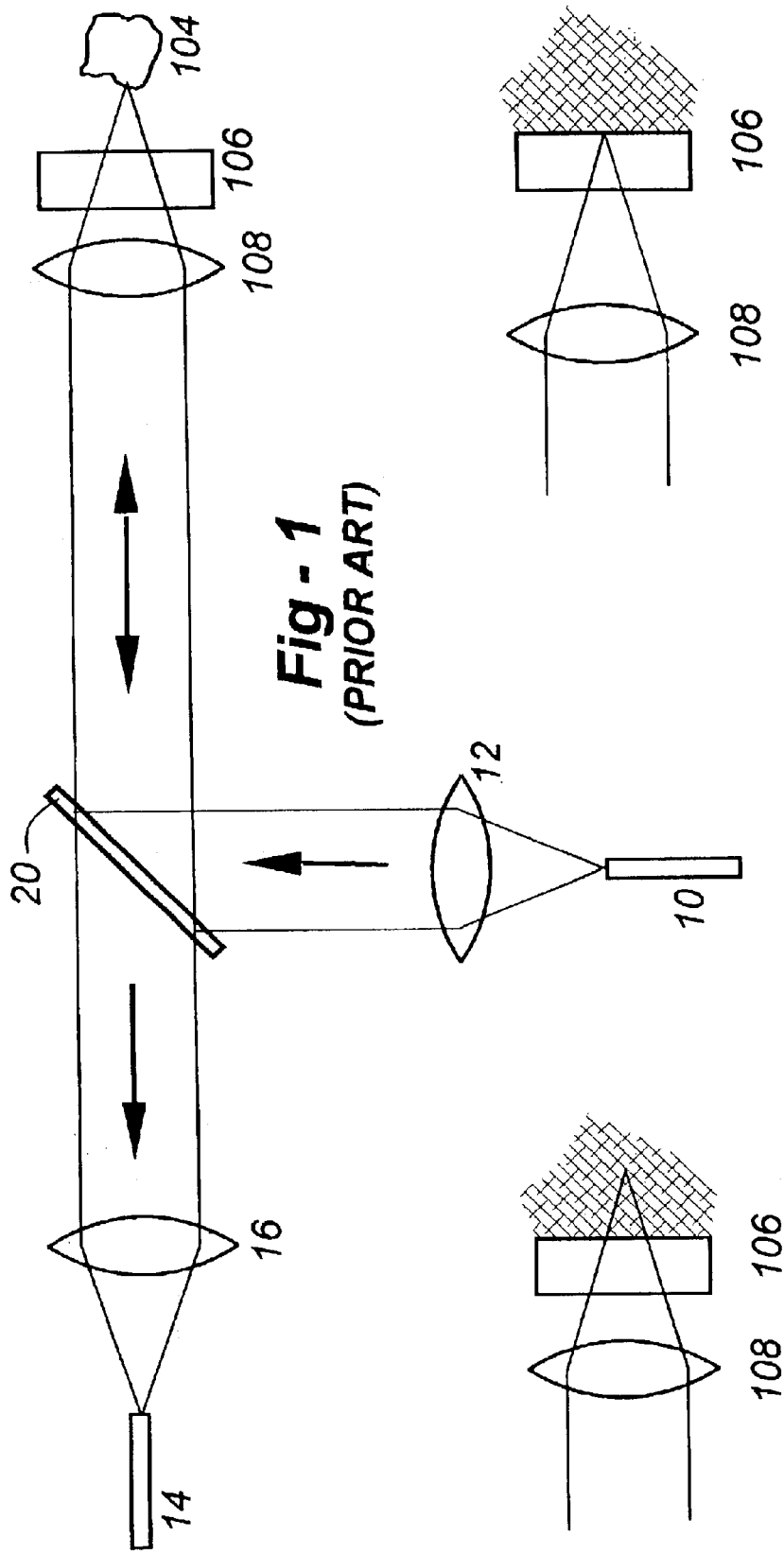

OPTICAL PROBE FOCUSING APPARATUS AND METHOD

REFERENCE TO RELATED APPLICATION

This application claims priority from U.S. Provisional Patent Application Ser. No. 60/351,731, filed Jan. 25, 2002, the entire content of which is incorporated herein by reference.

FIELD OF THE INVENTION

This invention relates generally to optical measurement probes and, in particular, to a method and apparatus for focusing such a probe.

BACKGROUND OF THE INVENTION

Induced radiative effects such as Raman scattering and fluorescence have become extremely valuable tools associated with the non-destructive determination of molecular constituents. Optical probes for such purposes are being employed in on-line process control in increasing numbers. These probes are often installed directly into the process stream or reactor, thus posing a potential safety hazard.

Free-space optical spectroscopy probes used in immersed applications typically involve imaging an optical sampling beam through a window bonded in the wall of a containment vessel. The window can be any material transparent to wavelengths of interest, though the most popular material being sapphire.

Many state-of-the-art spectroscopic fiber-optic probes used in laboratory and process analysis applications are based on confocal imaging. This is particularly true of laser-induced spectroscopy (including Raman), wherein the relayed optical images of both the fiber 10 carrying the excitation light and that of the collection fiber 14 are combined into a single probe beam by a combiner 20, as shown in the prior art arrangement of FIG. 1. The excitation and collection beams are respectively collimated and focused by elements 12 and 16, and the combined probe beam is focused by a lens 106 into/onto a sample 104, typically through window 106 which, again, is usually sapphire.

The position of the relayed, combined image of the fibers relative to the window is critical for some applications. In general, it is desirable to construct a probe whose fixed focal position is best suited to the largest cross-section of a particular application. There are two generally classes of samples: those which are transparent and those which are opaque. For transparent samples, it is best to focus at a point which is well into the material, shown in FIG. 2 as point 200. For opaque samples, however, it is advantageous to focus directly on the surface (at the window to sample interface), as shown in FIG. 3.

SUMMARY OF THE INVENTION

Broadly, this invention resides in a method of positioning a focused image within a sampled medium in a optical measurement probe of the type wherein a focused sampling image is transmitted through a window having a surface facing a sampled medium. According to the method, a test medium is measured, preferably through the window. The magnitude of an optical signal associated with the test medium is then compared to the magnitude of an optical signal associated with the window, and the result of the comparison is used to position the focused image. Typically, the magnitudes of optical signals are representative or Raman scattering or another wavelength-selective radiative sampling process such as fluorescence detection.

The method is not limited in terms of window composition, and is compatible with sapphire windows commonly used in industry. Nor is the invention limited in terms of test medium though, in the preferred embodiment a fluid hydrocarbon such as isopropyl alcohol is used. The signal comparison is preferably a ratio which may be used to position the focused image substantially proximate to the surface of the window for a sampled medium which is substantially opaque or away from the surface of the window for a sampled medium which is substantially transparent. As a further alternative, the magnitude of optical signal of the test medium and the magnitude of optical signal of the window may be roughly the same as a compromise to accommodate both opaque and transparent sampled media.

In many systems, a focusing lens is supported near the window, such that the step of using the result of the comparison to position the focused image includes moving the lens relative to the window to adjust the position of the focused image.

BRIEF DESCRIPTION OF THE DRAWINGS

FIG. 1 illustrates a typical, laser-induced fiber-optic spectroscopy system.

FIG. 2 is a simplified drawing that shows how, for transparent samples, it is best to focus at a point well past a process window; and FIG. 3 is a simplified drawing that shows how, for opaque samples, it is best to focus at a point near the surface of a process window.

DETAILED DESCRIPTION OF THE INVENTION

Broadly, this invention allows for the placement of a focused sampling image to be placed relative to a window easily and precisely. The method takes particular advantage the fact that when the sampling image is close to the window (sapphire, for example), the signal contains some amount of the sapphire signature.

According to the method, the probe is immersed into a known substance to obtain a ratio between the substance signal and that of the window material sapphire. In the preferred embodiment, the substance is clear hydrocarbon, such as isopropyl alcohol, though other substances may be used.

The ratio of the spectroscopic signal of the test medium to the spectroscopic signal of the window material is very sensitive to the position of the focused image. If a customer specifies a particular position, whether close to the surface of the window or deeper within the medium, the distance between the sample lens and window may be adjusted to obtain this position while observing the signal ratio. Conveniently, since a spacer is often used between the sample lens and window, the spaced may be selected or buffed down to particular thickness to achieve the desired result.

If a user does not know or care if the position of the focused images is near the window or deeper within the medium, it has been experimentally determined that, at least in the case of Raman spectroscopy, the position whereby one obtains 75 percent of the maximum potential alcohol signal also yields 75 percent of the maximum signal from an opaque sample in contact with the window. This optimal balance position, which represents a compromise between applicability to opaque and transparent samples, corresponds to a ratio of approximately 13:1 between the 953 cm-1 band of alcohol and 75 cm-1 band of sapphire.

We claim:

1. In a optical measurement probe of the type wherein a focused sampling image is transmitted through a window having a surface facing a sampled medium, a method of positioning the focused image within the sampled medium, comprising the steps of:

measuring a test medium;

comparing the magnitude of an optical signal associated with the test medium to the magnitude of an optical signal associated with the window; and using the result of the comparison to position the focused image.

2. The method of claim 1, wherein the window is a sapphire window.

3. The method of claim 1, wherein the test medium is a fluid hydrocarbon.

4. The method of claim 3, wherein the hydrocarbon is alcohol.

5. The method of claim 4, wherein the alcohol is isopropyl alcohol.

6. The method of claim 1, wherein the window is a sapphire window and the test medium is a substantially transparent fluid hydrocarbon.

7. The method of claim 1, wherein the comparison is used to position the focused image substantially proximate to the surface of the window for a sampled medium which is substantially opaque.

8. The method of claim 1, wherein the comparison is used to position the focused image away from the surface of the window for a sampled medium which is substantially transparent.

9. The method of claim 1, wherein the magnitude of optical signal of the test medium and the magnitude of optical signal of the window are roughly the same as a compromise to accommodate both opaque and transparent sampled media.

10. The method of claim 1, wherein the magnitudes of optical signals are representative or Raman scattering or another wavelength-selective radiative sampling process.

11. The method of claim 1, including a focusing lens supported near the window, and wherein the step of using the result of the comparison to position the focused image includes moving the lens relative to the window to adjust the position of the focused image.

12. In an optically induced radiative measurement probe of the type wherein a focused sampling image is transmitted through a window having a surface facing a sampled medium, a method of positioning the focused image within the sampled medium, comprising the steps of:

measuring a test medium through the window;

comparing the magnitude of a Raman or fluorescent signal associated with the test medium to the magnitude of a Raman or fluorescent signal associated with the window to obtain a signal ratio; and using the ratio to position the focused image.

13. The method of claim 12, wherein the window is a sapphire window.

14. The method of claim 12, wherein the test medium is a fluid hydrocarbon.

15. The method of claim 14, wherein the hydrocarbon is alcohol.

16. The method of claim 15, wherein the alcohol is isopropyl alcohol.

17. The method of claim 12, wherein the window is a sapphire window and the test medium is a substantially transparent fluid hydrocarbon.

18. The method of claim 12, wherein the comparison is used to position the focused image substantially proximate to the surface of the window for a sampled medium which is substantially opaque.

19. The method of claim 12, wherein the comparison is used to position the focused image away from the surface of the window for a sampled medium which is substantially transparent.

20. The method of claim 12, wherein the magnitude of optical signal of the test medium and the magnitude of optical signal of the window are roughly the same as a compromise to accommodate both opaque and transparent sampled media.

21. The method of claim 12, including a focusing lens supported near the window, and wherein the step of using the result of the comparison to position the focused image includes moving the lens relative to the window to adjust the position of the focused image.

* * * * *